United States Patent [19]

Hutson

[11] 4,114,422

[45] Sep. 19, 1978

[54] METHOD OF MONITORING DIET

[76] Inventor: Donald G. Hutson, 101 W. Nevin, Richmond, Calif. 94804

[21] Appl. No.: 537,911

[22] Filed: Jan. 2, 1975

[51] Int. Cl.$^2$ ............................................. G01N 31/08
[52] U.S. Cl. .................................... 73/23.1; 23/230 B
[58] Field of Search ................ 73/23.1, 23; 23/232 C, 23/232 R, 254 R, 230 B

[56] References Cited

U.S. PATENT DOCUMENTS

| 3,338,087 | 8/1967 | Moberg et al. | 73/23 |
| 3,676,649 | 7/1972 | Burk | 73/23.1 |

OTHER PUBLICATIONS

Larsson; *Acta. Chem. Scand.*, "Gas Chrom. of Organic Volatiles in Human Breath and Saliva", 19(1965) pp. 159-164.
Freund; *Biochemical Factors in Alcoholism*, "Serial Determinations of Acetaldehyde and Acetone in Alveolarair", 1967, pp. 89-95.
Klatt et al.; *Chem. Instrumentations;* "An Inexpensive Digital Integrator for Gas Chrom.", 3(4) pp. 327-331 (1972).
Atkins; *"Dr. Atkins' Diet Revolution"*; pp. 126-129, 1972.

*Primary Examiner*—Richard C. Queisser
*Assistant Examiner*—Stephen A. Kreitman
*Attorney, Agent, or Firm*—Polster, Polster and Lucchesi

[57] ABSTRACT

A method of monitoring diet includes introducing a sample of aveolar air into a device capable of measuring acetone quantitatively in amounts at least as small as 0.3 mcgm/l (microgram per liter); measuring the amount of acetone in the sample; converting the measurement into immediately recognizable humanly intelligible form, and displaying the measurement in that form within a period of no more than five minutes after the sample is introduced into the device.

1 Claim, 1 Drawing Figure

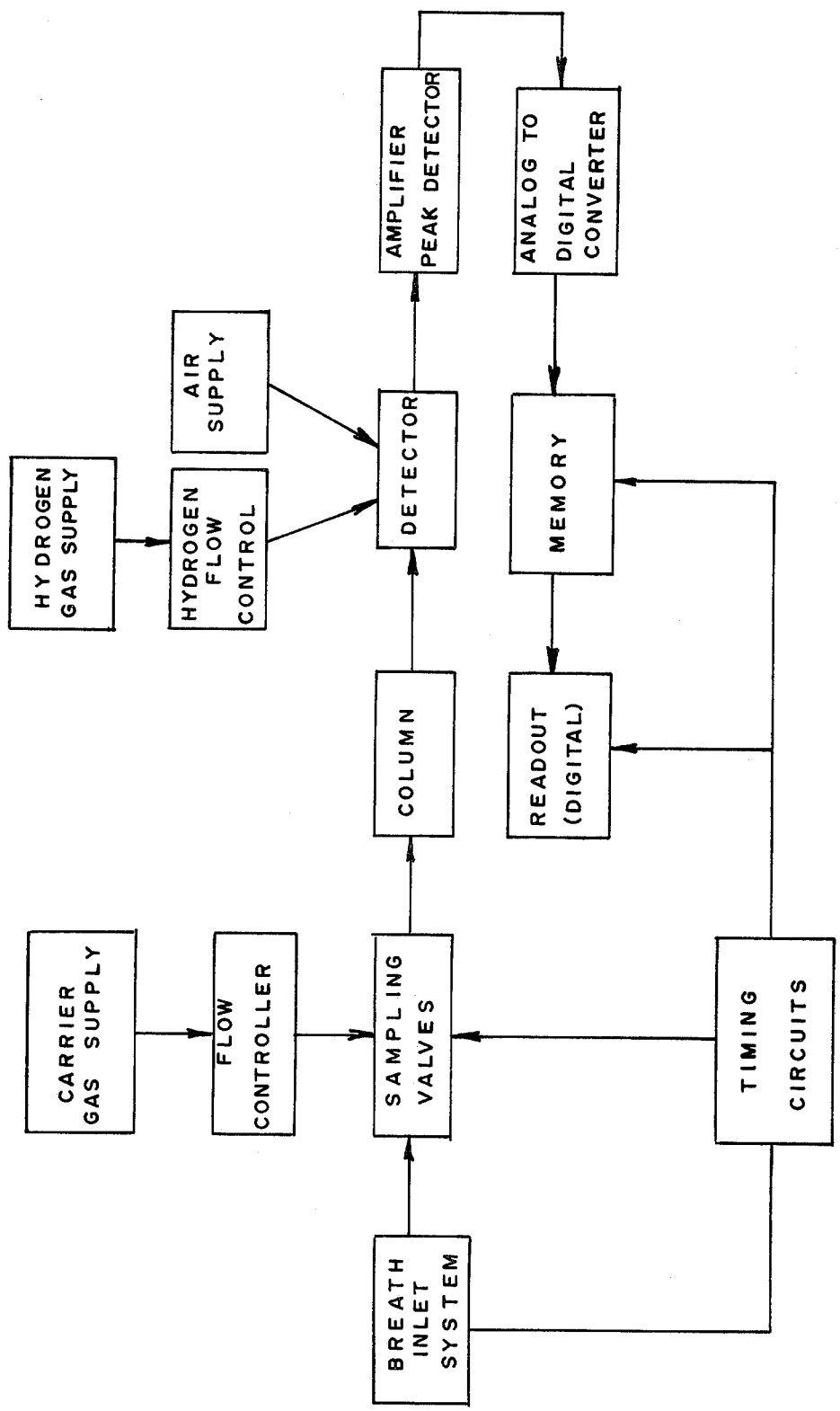

METHOD OF MONITORING DIET

BACKGROUND OF THE INVENTION

For a variety of reasons, primarily health, many people in the United States are concerned with achieving and maintaining a particular body weight or range of body weights. Most of these people are concerned about being overweight, and want to reduce. A few are underweight and want to gain. In some areas, particularly California, there are weight control clinics, in which large numbers of patients are checked, counselled, and prescribed for every day.

One of the chief problems associated with achieving and maintaining a particular desired weight is the inclination of the dieter to stray from the diet, an inclination which frequently proves so strong as to lead the dieter to try to deceive not only the doctor, but himself. It is standard practice in weight control regimes now commonly employed to give the dieter a diary and ask that he record immediately everything that he ingests. In practice, it is found that, especially among the obese, the dieter's recall in inaccurate, and he is likely not to be truthful or conscientious in his keeping of the diary. Furthermore, if a person, even a doctor, is a friend of the dieter, that person may not always be truthful either, so as not to embarrass the patient. The dieter frequently becomes discouraged, and understandably, when he has been faithful to the diet and still shows a weight gain which may in fact be the result of water retention. There has been no positive method of determining when dieters have strayed briefly from their diets, and, as has been observed, the weight of a person from day to day varies without any immediate relation to the amount of food he ingests.

It has long been suspected that free acetone is a physiological metabolite. It has been known for many years that diabetics have high levels of blood acetone, and corresponding high levels of acetone in the breath. In uncontrolled but non-comatose diabetics, blood acetone levels range to 75mg%, equal to 2,263mcgm/l in the breath. In 1952 Henderson, Karger and Wrenshall, of the University of Toronto, published a paper in *Diabetes*, Volume I, No. 3, in which they reported among other observations relating to diabetics, that increases in weight are accompanied by a decrease in acetone exhalation and decreases in weight, by an increase in acetone exhalation.

It is believed that ketones are normal intermediates of fat metabolism, generating small amounts of acetoacetate and 3 hydroxybutyrate. Acetone is formed by the spontaneous and non-enzymatic decarboxylation of acetoacetate. If there is not adequate oxaloacetate from carbohydrates to maintain the Krebs Cycle efficiently, the active acetate from fat is diverted to form ketone bodies which give rise to increased amounts of free acetone. The body oxidizes selectively alcohol, carbohydrates and fats, in that order. Accordingly, the amount of acetone in the blood is a function of fat metabolism. It will increase with exercise, or a diet low in carbohydrates. It will decrease with the ingestion of alcohol or carbohydrates.

The normal acetone content of the blood varies from person to person, so that some norm must be established for each person, but once that is established a deviation from that norm will indicate a deviation in the fat metabolism.

Breath acetone levels from deep lung (aveolar) breath are directly proportional to the acetone levels in the blood. 330cc of deep lung air contain the same amount of acetone as 1cc of blood. However, the amounts involved are so small that there has been no effective way to use the information which has been suggested by researchers in the field.

Even when instruments were devised which were able to detect and measure very small amounts of acetone, variations in breath acetone might constitute an interesting adjunct to the tools used by the doctor, but it would not suggest a method of monitoring diet which would in itself induce compliance with a regimen set for the dieter.

One of the objects of this invention is to provide a method of monitoring the diet which involves an accurate measure of fat loss, which reinforces the dieter's determination, rewarding faithfulness and discouraging cheating.

Another object is to provide such a method which is simple, safe, and quick, saving the time of both the dieter and the physician.

Other objects will become apparent to those skilled in the art in the light of the following description and accompanying drawings.

SUMMARY OF THE INVENTION

In accordance with this invention, generally stated, a method of monitoring diet is provided by which a dieter is given an accurate measure of fat loss or gain, is encouraged to maintain the diet both by the reward of immediately recognized accomplishment and the punishment of an immediately detected lapse from the diet. The method includes introducing a sample of aveolar air into a device, such as a gas chromatograph with hydrogen flame ionization detector, capable of measuring acetone quantitatively in amounts at least as small as 0.3 mcgm/l; measuring the amount of acetone in the sample; converting the measurement into immediately humanly intelligible form and displaying the measurement in that form within a period of 5 minutes after the sample is introduced into the device.

The method of this invention can also include the additional step of measuring the amount of ethyl alcohol in the sample, converting that measurement into humanly intelligible form and displaying that measurement in that form in at least one of time and place different from the display of the measurement of acetone.

The term "display" is used herein to indicate the presentation of the measurement in any form which can be grasped immediately, including read-out, print-out, audible message, or even graph form, although the particular type of read-out of the preferred embodiment has distinct advantages.

BRIEF DESCRIPTION OF THE DRAWING

In the drawing FIG. 1 is a diagrammatic representation of apparatus suitable for use in the method of this invention.

DESCRIPTION OF THE PREFERRED EMBODIMENT

Normal, non-dieting women have a higher breath and blood acetone level than men, but, as distinguished from diabetics, the breath acetone level in normal non-dieting persons will in any event vary only between 0.9mcgm/l and 3.0mcgm/l (in terms of blood levels 0.03mg% to 0.10mg%). In the method of this invention, therefore, it is necessary to detect and to measure very small amounts of acetone in the breath. To that end, the preferred measuring instrument is a gas chromatograph with hydrogen flame ionization detector, such as is commercially available, under the trademark DIET MONITOR MARK III, from Cal Detect, Inc., 101 North Nevin Avenue, Richmond, Calif., the operation of which is substantially the same as that of the Varian Aerograph Series 1400 gas chromatograph, a rather complete description of which is found in Varian Aerograph's publication No. 85-001065-00, printed September, 1969, and copyrighted 1969 by Varian Aerograph.

In addition, however, as indicated in the drawing FIG. 1, and as in the Diet Monitor Mark III, the output signal from the detector is fed to an amplifier-peak detector, hence to an analog to digital converter, to a memory circuit and thence to a digital read-out.

A breath sample is introduced to the device by having the person to be tested blow into a tube connected to the instrument by way of a sampling mechanism, solenoid operated to take a precisely measured 2cc sample after a certain length of time following the beginning of the blowing, to ensure that the sample is taken from deep lung aveolar breath. The sampler can be essentially an automated version of a kind of device described in the U.S. patent to Molberg et al U.S. Pat. No. 3,338,087.

The preferred embodiment of method of this invention comprises the steps of introducing to the gas chromatograph aveolar breath, by blowing through a tube connected to the sampling device; measuring quantitatively the amount of acetone in the resulting sample, which in the preferred embodiment is accomplished by the gas chromatograph as described; converting the measurement into immediately humanly intelligible form, which in this embodiment involves converting the output signal from the chromatograph to digital form, and displaying the measurement in that form within a period of five minutes after the sample is introduced into the device, which, in the preferred embodiment, takes the form of displaying the numbers generated in the digital converter on a read-out display large enough and bright enough to enable the person being tested to read the numbers clearly and immediately. Preferably, the analog to digital converter is so programmed that the read-out is expressed in numbers representing blood acetone level in milligram percent. The absolute numbers are of no particular significance to the subject, but blood levels expressed in milligram percent represent standard units to the physician. In the preferred embodiment, the numbers are displayed as they are being generated, so that there is a continuous "movement" of numbers until the peak is reached in approximately forty-five seconds. This has been found to be important, because it heightens the excitement generated in the person being tested. It has been found that, particularly with the movement of numbers, the reaching of a high number, which indicates that a relatively high amount of body fat is being "burned," produces a strong feeling of accomplishment and euphoria, while the attainment of only a low total has a chastening effect, particularly since it usually represents a lapse from the prescribed regimen.

The display of the results within a short length of time is also important to this method. A display within less than a minute, but with at least fifteen seconds delay is ideal, because it combines a certain amount of suspense with sufficiently quick results to avoid impatience or a wandering of attention. It also permits heavy utilization of the instrument.

To heighten the psychological effect, it is desirable to provide sensitivity controls for the instrument which will provide at least two and preferably at least three base levels. Suitable circuitry for producing amplitudes in multiples of 10, 20 and 30 times, for example, is standard in the art. Patients are likely either to try to get a look at other patients' readings or to compare notes. As has been indicated, the normal level of breath acetone is likely to vary by a factor of about 30 although the vast majority of "normal" persons lie in the 0.10mg% to 2.0mg% range, a factor of 20. Accordingly, those with normally low acetone levels may well be satisfying the requirements of a diet when the acetone level of their breath has increased ten times, and still have a breath level markedly below that of a person with a much higher normal breath acetone level, who is doing unsatisfactorily. Therefore, it is desirable to try to produce a read-out of approximately the same magnitude for the patients with the various magnitudes of normal acetone levels. If three levels of sensitivity of the instrument can be used which produce multiplications of 1, 10 and 20, for example, the doctor can at least provide such a read-out in most normal patients.

In the preferred embodiment of the method of this invention, still another step includes measuring, in the same sample, the alcohol content and displaying it, in digital form, in terms of the blood alcohol content in milligram percent. The display may be at a different place from the display of the acetone content, either immediately adjacent it or at some place remote therefrom, or at a different time from the display of the acetone content, or both.

The display of the alcohol content of the blood serves to point up the effect that drinking has on fat metabolism, to give the physician an indication of the amount of alcohol being ingested, and, with respect to one who has not been drinking, affirm that fact.

A person adhering to a low-carbohydrate diet will ordinarily double his breath acetone level by the second day of the diet and if carbohydrates are completely eliminated may increase the level by a factor of from five to ten in that time. By the third or fourth day the acetone level of a person on a low-carbohydrate diet is likely to have increased by a factor of 100 to 200, and will generally level off, at the high level, by the seventh or eighth day.

Once the subject's stable acetone level has been reached, it is a simple matter to detect when he goes off his diet. The eating of a donut, for example, will cause the reading to drop 15 percent within 3 hours, and to continue to drop until the body has metabolized all the carbohydrates. The ingestion of alcohol will also become apparent quickly, because of the preferential metabolism of the alcohol by the body, and the effects will persist long enough to be detectable. Thus, if on a weekend, a subject eats and drinks beyond the limits prescribed, the method of this invention will betray the lapse if a test is run near the beginning of the following week.

Preferably, the acetone and alcohol levels are tested daily, with gaps, if any, only at weekends.

Among the advantages of this invention for the physician who should be attending a person on a drastically reduced diet are the following:

1. It provides an almost fool-proof method of determining whether the patient is staying on the diet.

2. It gives the physician an instrument that can be used to evaluate slight changes in the patient's diet, such as determining the effect of refined carbohydrates added to or taken away from the diet, etc. 3. It gives the physician a psychological advantage since the patient knows the instrument will tell him when he has gone off his diet, and the standard excuses such as water retention, etc. cannot be used.

4. The analysis is quick and simple. The subject blows, an analysis button is pressed, and the rest is automatic — 45 seconds later the acetone reading is computed and displayed on a digital read-out. The subject's blood alcohol reading is also stored in the memory for later recall if desired.

5. The method also serves as a screening device to detect diabetes or other metabolic disorders, and can, or course, be used in the monitoring of the progress of such disorders.

6. The method may also be used to measure total body water by having the subject ingest a known amount of alcohol and measuring the alcohol in the deep lung air, this value being inversely proportional to the body water content (i.e., alcohol distributes on basis of the body water).

7. This method also can be used to measure total body fat by giving the subject a "cocktail" of alcohol and acetone. Alcohol distributes only in the body water whereas acetone distributes in both body water and body fat. The alcohol reading is used to determine the total body water and the ratio of alcohol reading to acetone reading gives a measure of water to water plus fat. By using a suitable conversion table, the total body fat may be determined.

Among the advantages the method gives to the patient are the following:

1. It allows the patient to see progress within 24 hours after starting his diet.

2. Any decrease in his acetone reading occurs so quickly when he goes off his diet that it will normally be possible for him to decide which meal caused the decrease in the acetone readings.

3. Overall, it teaches him the effect of various foods on his weight control problem.

4. It teaches him to be more concerned with what he eats rather than with watching the scale.

As has been indicated, it is desirable to establish the initial acetone level before a patient is placed on a low-carbohydrate diet. If the person is normal and has not been on any restricted diet, the instrument will usually give acetone readings of 0.04 to 0.14mg%. Readings at the low end usually indicate that the patient has a high carbohydrate intake, is physically inactive, has recently consumed alcohol, or has low metabolism or faulty metabolism, and is likely to have more difficulty losing weight than a person with a higher normal acetone level. Higher readings indicate that the patient has a moderate carbohydrate intake, is physically active, has a high basic metabolism, or may be diabetic, particularly if the readings are greater than 0.30mg%.

A typical actual set of readings of a person on a 1500 calorie diet is as follows:

| Day 1 | Before starting diet Diet started in the morning | .10 mg% | (Baseline morning) |
|---|---|---|---|
| | Afternoon | .16 mg% | (Baseline for the afternoon was .12 mg%) |
| Day 2 | Morning | .24 | |
| Day 3 | Morning | .38 | |
| Day 4 | Morning | .72 | |
| Day 5 | Morning | 1.85 | |
| Day 6 | Weekend not monitored | | |
| Day 7 | | | |
| Day 8 | | .08 | Alcohol consumed on Sunday |
| Day 9 | Back on diet | .16 | |
| Day 10 | | .32 | |
| Day 11 | | .59 | |
| Day 12 | | .132 | |
| Day 13 | | .201 | |

What is significant to the patient and doctor in this and every case, is not so much the absolute figures but the relation of the figures to the established base line. As long as the acetone reading is higher than the normal base line, the patient is metabolizing fat at a greater rate than he normally does.

Numerous variations in the method of this invention within the scope of the appended claims will occur to those skilled in the art in the light of the foregoing disclosure. Merely by way of illustration, a gas chromatograph with an Argon ionization detector can be used, although it is not as sensitive as the hydrogen flame ionization detector. As has been indicated, the display can take the form of a print-out for a permanent record or even an audible message. It can be in graph or chart form. However, as has been explained, the preferred method has numerous advantages. The display can be in any desired units, the milligram percent being the preferred units to permit immediate correlation with standard blood studies in which the contents of the blood are expressed in terms of milligram percent. Other sampling systems can be used, although the one described is effective and desirable. These are merely illustrative.

Having thus described the invention, what is claimed and desired to be secured by Letters Patent is:

1. The method of determining total body fat of a human subject comprising introducing a sample of alveolar air from said subject into a device capable of measuring both acetone and alcohol quantitatively in amounts at least as small as 1 microgram per liter and measuring the amount of alcohol and acetone in said sample to establish a base measure; introducing into said subject exactly known and predetermined amounts of alcohol and acetone, permitting said alcohol and acetone to be distributed through the water and fat of said subject, introducing another sample of alveolar air from said subject into said measuring device, measuring the amount of alcohol and acetone in said sample, determining the ratio of alcohol to acetone attributable to said introduced amounts of alcohol and acetone in the said alveolar air, and computing therefrom the total body fat of said subject.

* * * * *